US010026335B2

(12) United States Patent
White et al.

(10) Patent No.: US 10,026,335 B2
(45) Date of Patent: *Jul. 17, 2018

(54) ACTIVITY RECOGNITION WITH ACTIVITY REMINDERS

(71) Applicant: NIKE, Inc., Beaverton, OR (US)

(72) Inventors: Kristen L. White, Portland, OR (US); Michael L. Orenstein, Portland, OR (US); Jenny Campbell, Beaverton, OR (US); Christina S. Self, Portland, OR (US); Elizabeth Walker, Portland, OR (US); Marco Micheletti, Seattle, WA (US); Greg McKeag, Seattle, WA (US); James Zipperer, Seattle, WA (US); Michael Lapinsky, Seattle, WA (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/609,427

(22) Filed: May 31, 2017

(65) Prior Publication Data

US 2017/0263148 A1   Sep. 14, 2017

Related U.S. Application Data

(63) Continuation of application No. 15/427,835, filed on Feb. 8, 2017, which is a continuation of application
(Continued)

(51) Int. Cl.
*G08B 21/24*   (2006.01)
*G09B 19/00*   (2006.01)
(Continued)

(52) U.S. Cl.
CPC ........ *G09B 19/0038* (2013.01); *A43B 3/0005* (2013.01); *A43B 5/00* (2013.01);
(Continued)

(58) Field of Classification Search
CPC ....... A61B 5/1118; A61B 5/002; A63B 24/00; A63B 24/0622; A63B 71/0622;
(Continued)

(56) References Cited

U.S. PATENT DOCUMENTS

| 5,387,164 A | 2/1995 | Brown, Jr. |
| 7,698,101 B2 | 4/2010 | Alten et al. |

(Continued)

FOREIGN PATENT DOCUMENTS

| CN | 102804238 A | 11/2012 |
| CN | 103154954 A | 6/2013 |

(Continued)

OTHER PUBLICATIONS

Dec. 15, 2014 (WO)—ISR—App. No. PCT/US2014/050154.
Jan. 19, 2015(WO)—ISR—App. No. PCT/US2014/050168.
Jan. 19, 2015 (WO)—ISR—App. No. PCT/US2014/0501736.

Primary Examiner — Hung T Nguyen
(74) Attorney, Agent, or Firm — Banner & Witcoff, Ltd.

(57) ABSTRACT

An athletic performance monitoring system, for motivating a user to reach a goal level of athletic activity. The system may motivate the user by calculation a deficit between a current total level of activity and the goal level of athletic activity, and suggesting activity types that the user may carry out an order to reach the goal level, wherein the suggested activity types may be based on activities that are geographically close to the user, or sporting equipment worn by, or in possession of, the user.

20 Claims, 8 Drawing Sheets

Related U.S. Application Data

No. 14/194,161, filed on Feb. 28, 2014, now Pat. No. 9,595,180.

(60) Provisional application No. 61/869,617, filed on Aug. 23, 2013, provisional application No. 61/863,259, filed on Aug. 7, 2013.

(51) Int. Cl.
*G09B 5/02* (2006.01)
*A43B 5/00* (2006.01)
*A43B 3/00* (2006.01)
*A63B 24/00* (2006.01)
*A63B 71/06* (2006.01)

(52) U.S. Cl.
CPC ...... *A63B 24/0062* (2013.01); *A63B 71/0622* (2013.01); *G08B 21/24* (2013.01); *G09B 5/02* (2013.01); *A63B 2220/53* (2013.01); *A63B 2220/56* (2013.01); *A63B 2220/62* (2013.01); *A63B 2220/803* (2013.01); *A63B 2220/836* (2013.01); *A63B 2225/50* (2013.01); *A63B 2230/06* (2013.01); *A63B 2230/207* (2013.01); *A63B 2230/65* (2013.01); *A63B 2230/75* (2013.01)

(58) Field of Classification Search
CPC .......... A63B 2220/803; G06F 19/3481; G08B 21/24; G01C 21/20; G09B 19/0038
USPC ... 340/539.1, 539.11, 539.12, 539.13, 573.1, 340/573.4; 434/236; 600/300, 301
See application file for complete search history.

(56) References Cited

U.S. PATENT DOCUMENTS

| | | | |
|---|---|---|---|
| 7,771,320 B2 | 8/2010 | Riley et al. | |
| 7,894,849 B2 | 2/2011 | Kass et al. | |
| 7,927,253 B2 | 4/2011 | Vincent et al. | |
| 8,125,314 B2 | 2/2012 | Fithian et al. | |
| 9,053,509 B2 | 6/2015 | Azose | |
| 9,171,445 B2* | 10/2015 | Nishihara | G08B 21/0415 |
| 9,589,445 B2 | 3/2017 | White et al. | |
| 2003/0226695 A1 | 12/2003 | Mault | |
| 2005/0286686 A1 | 12/2005 | Krstulich | |
| 2006/0020174 A1 | 1/2006 | Matsumura et al. | |
| 2007/0072156 A1 | 3/2007 | Kaufman et al. | |
| 2008/0086318 A1 | 4/2008 | Gilley et al. | |
| 2008/0096726 A1 | 4/2008 | Riley et al. | |
| 2009/0047645 A1 | 2/2009 | Dibenedetto et al. | |
| 2009/0048044 A1 | 2/2009 | Oleson et al. | |
| 2009/0093341 A1 | 4/2009 | James et al. | |
| 2009/0189982 A1 | 7/2009 | Tawiah | |
| 2009/0233771 A1 | 9/2009 | Quatrochi et al. | |
| 2009/0258710 A1 | 10/2009 | Quatrochi et al. | |
| 2010/0048358 A1 | 2/2010 | Tchao et al. | |
| 2010/0105525 A1 | 4/2010 | Thukral et al. | |
| 2010/0273610 A1* | 10/2010 | Johnson | H04M 1/72569 482/9 |
| 2011/0131005 A1 | 6/2011 | Ueshima et al. | |
| 2011/0197157 A1 | 8/2011 | Hoffman et al. | |
| 2012/0015778 A1 | 1/2012 | Lee et al. | |
| 2012/0028355 A1 | 2/2012 | Sato et al. | |
| 2012/0083705 A1 | 4/2012 | Yuen et al. | |
| 2012/0253485 A1 | 10/2012 | Weast et al. | |
| 2012/0283855 A1 | 11/2012 | Hoffman et al. | |
| 2012/0313776 A1 | 12/2012 | Utter, II | |
| 2013/0073388 A1 | 3/2013 | Heath | |
| 2013/0197679 A1 | 8/2013 | Balakrishnan et al. | |
| 2013/0254329 A1 | 9/2013 | Lin et al. | |
| 2014/0085077 A1 | 3/2014 | Luna et al. | |
| 2014/0212855 A1 | 7/2014 | Robinson | |
| 2015/0066172 A1 | 3/2015 | Yi | |
| 2017/0080288 A1* | 3/2017 | Roh | A63B 24/0075 |

FOREIGN PATENT DOCUMENTS

| | | |
|---|---|---|
| EP | 2357450 A2 | 8/2011 |
| JP | 2001231904 A | 8/2001 |
| JP | 2004118339 A | 4/2004 |
| JP | 2011189014 A | 9/2011 |
| WO | 2012061438 A2 | 5/2012 |
| WO | 2013109780 A2 | 7/2013 |
| WO | 2013109916 A1 | 7/2013 |

* cited by examiner

US 10,026,335 B2

ACTIVITY RECOGNITION WITH ACTIVITY REMINDERS

CROSS REFERENCE TO RELATED APPLICATIONS

This application is a continuation of U.S. patent application Ser. No. 15/427,835, filed Feb. 8, 2017, which is a continuation of U.S. patent application Ser. No. 14/194,161, filed Feb. 28, 2014, now U.S. Pat. No. 9,595,180, which claims the benefit of, and priority to, U.S. Provisional Patent Application No. 61/863,259 filed Aug. 7, 2013, and U.S. Provisional Application No. 61/869,617 filed Aug. 23, 2013. The contents of all of the above listed applications are expressly incorporated herein by reference in their entirety for any and all non-limiting purposes.

BACKGROUND

Exercise and fitness have become increasingly popular and the benefits from such activities are well known. Various types of technology have been incorporated into fitness and other athletic activities. For example, a wide variety of portable electronic devices are available for use in fitness activity such as MP3 or other audio players, radios, portable televisions, DVD players, or other video playing devices, watches, GPS systems, pedometers, mobile telephones, pagers, beepers, etc. Many fitness enthusiasts or athletes use one or more of these devices when exercising or training to keep them entertained, provide performance data or to keep them in contact with others, etc. Such users have also demonstrated an interest in recording their athletic activities and metrics associated therewith. Accordingly, various sensors may be used to detect, store and/or transmit athletic performance information. Oftentimes, however, athletic performance information is presented in a vacuum or based on the overall athletic activity. Exercisers may be interested in obtaining additional information about their workouts, or daily activity.

Aspects of this disclosure are directed towards novel systems and methods that address one or more of these deficiencies. Further aspects relate to minimizing other shortcomings in the art.

SUMMARY

The following presents a simplified summary of the present disclosure in order to provide a basic understanding of some aspects of the invention. This summary is not an extensive overview of the invention. It is not intended to identify key or critical elements of the invention or to delineate the scope of the invention. The following summary merely presents some concepts of the invention in a simplified form as a prelude to the more detailed description provided below.

Aspects of the systems and methods described herein relate to a computer-implemented method of operating a device. The device may receive the location of a user, and additionally, calculate a deficit between a level of activity performed by the user and a goal level of activity. Using the calculated deficit, the device suggests one or more activity types geographically close to the user which may be carried out to reach the goal level of activity.

In another aspect, this disclosure relates to a non-transitory computer-readable media with computer-executable instructions that when executed by a processor is configured to calculate a deficit between a level of activity performed by a user and a goal level of activity, in addition to determining athletic equipment available to the user. Using the calculated deficit, in addition to the information about the athletic equipment available to the user, the processor suggests one or more activity types to be carried out by the user to reach the goal level of activity.

This Summary is provided to introduce a selection of concepts in a simplified form that are further described below in the Detailed Description. The Summary is not intended to identify key features or essential features of the claimed subject matter, nor is it intended to be used to limit the scope of the claimed subject matter.

DETAILED DESCRIPTION

Aspects of this disclosure relate to systems and methods for providing an athlete, or user, with information related to his/her daily physical activity. In one embodiment, this user activity information may include information related to a user's cumulative daily activity, and a comparison of this cumulative daily activity to one or more daily activity goals. In another aspect, the activity information may include instructions, suggestions, or tips as to how a user may supplement his/her daily activity in order to reach a daily activity level goal. In other aspects, the systems and methods described herein consider activities performed by a user/athlete on timescales other than daily activity, and may include hourly, weekly, monthly, or yearly activity levels, or any other timescale of interest to a user performing activities.

In order to monitor, analyze, and provide feedback on activities being performed by a user, athletic data may be recorded from one or more sensors receiving information related to one or more activities being carried out by the user. The athletic data may be actively or passively sensed and/or stored in one or more non-transitory storage mediums, and used to generate an output, such as for example, calculated athletic attributes, feedback signals to provide guidance, and/or other information. These, and other aspects, will be discussed in the context of the following illustrative examples of a personal training system.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
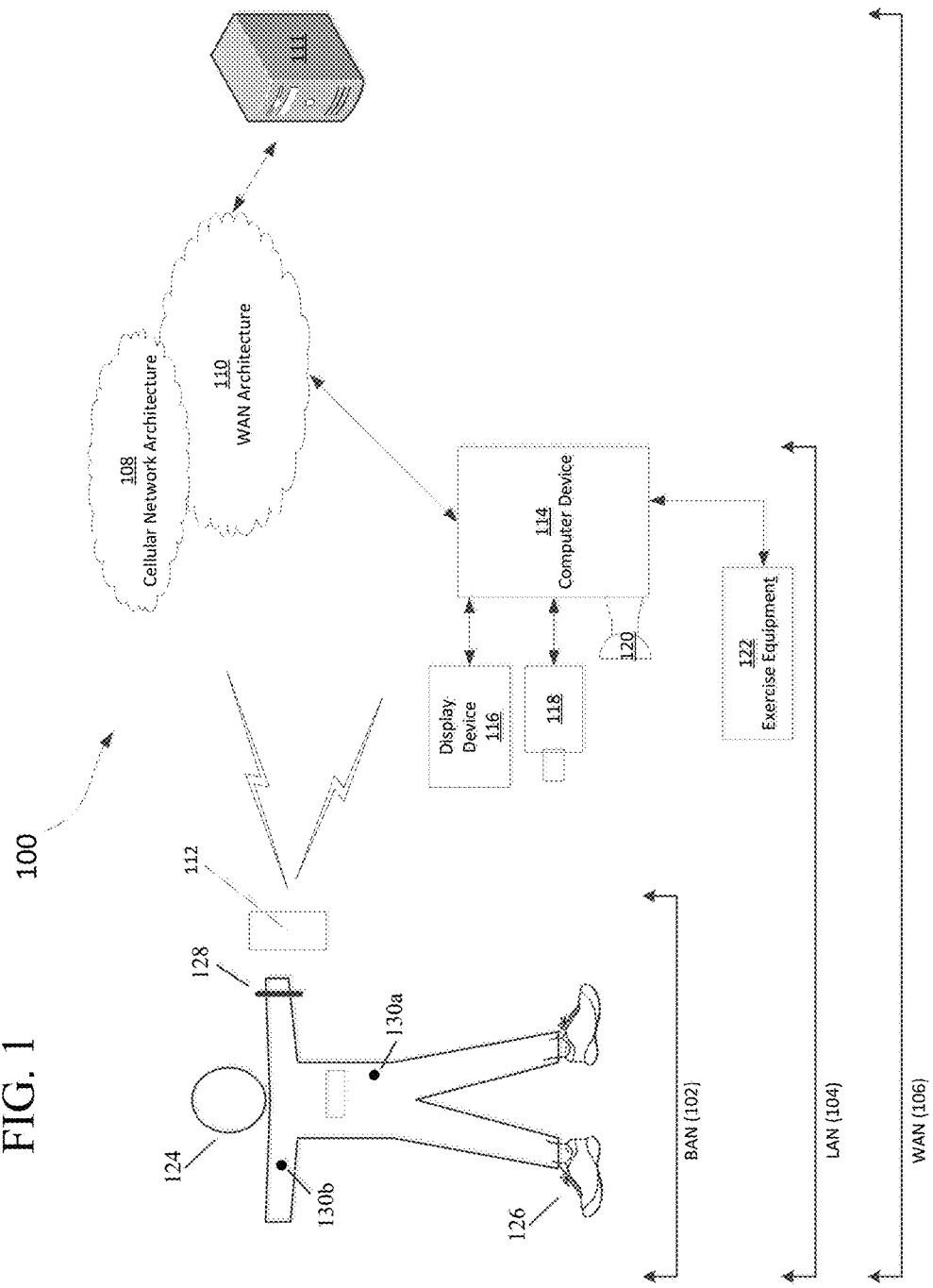
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
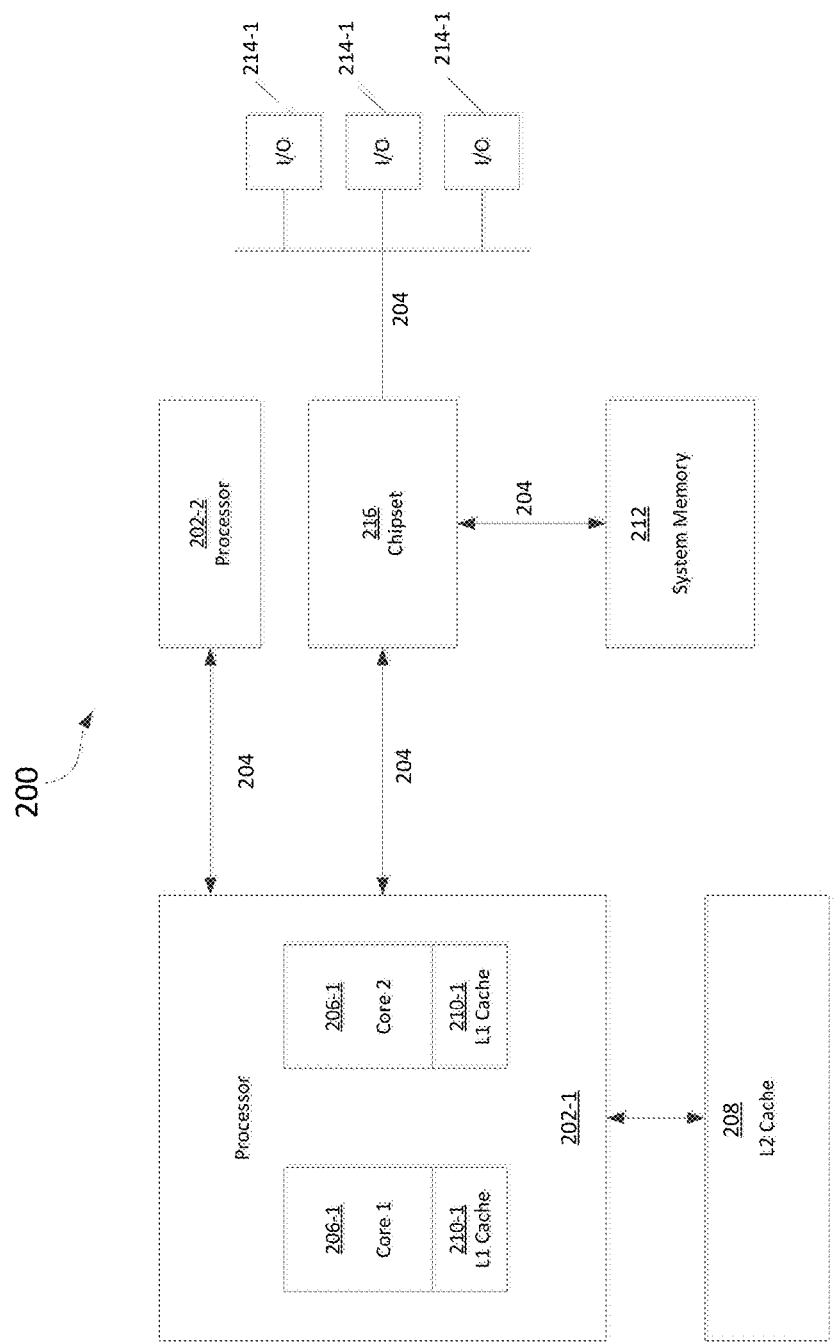
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, or motion data, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points (otherwise referred to as activity points, or as a level of activity), to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 118 and/or sensor 128 may comprise one or more thermal imaging devices. In one embodiment, image-capturing device 118 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
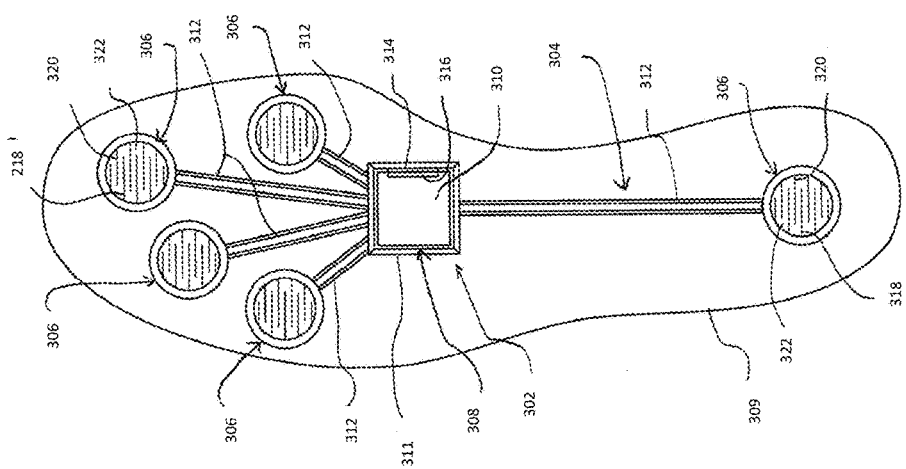
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance" may be measured, which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
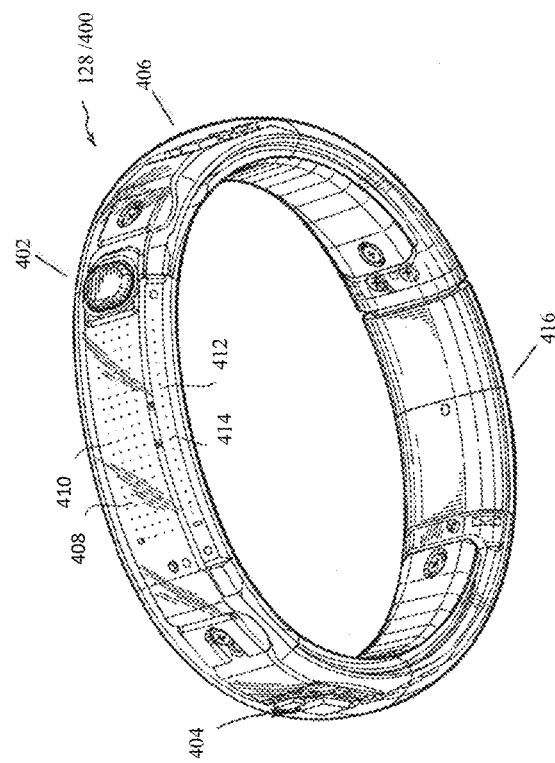
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
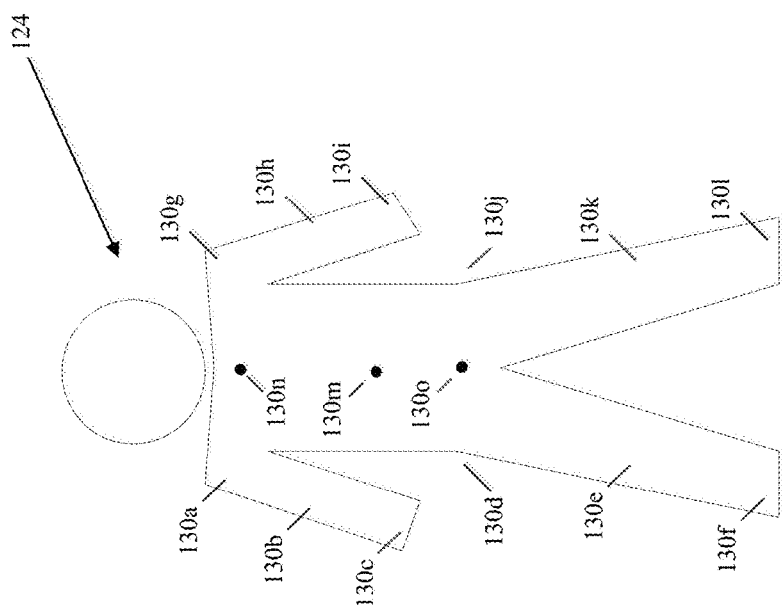
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-1306o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 130n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 130m-130o may serve as a point for a center of moment location of user 124. In another embodiment, one or more locations may serve as a center of moment of specific body parts or regions.

Figure 6:
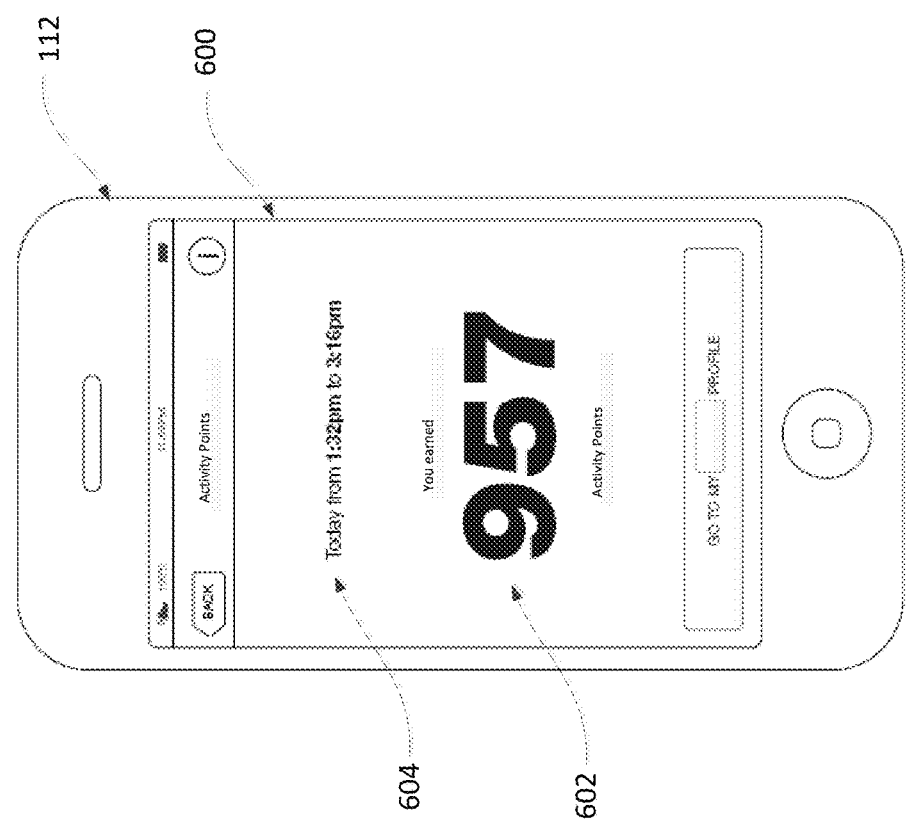
FIG. 6 depicts an example display of a graphical user interface informing a user of a cumulative number of activity points earned.

FIG. 6 depicts an example display of a graphical user interface (GUI) informing a user of a cumulative number of activity points, or energy expenditure points, earned during a specified time period. As discussed in relation to FIG. 1, system 100 may execute one or more processes to calculate activity points associated with one or more activities carried out by a user. In one embodiment, activity points relate to calories burned by a user during physical activity, however any quantifiable feature of an activity may be used by system 100 to calculate activity points. These features may include, among others, a total time spent performing a given activity, a total distance traveled during an activity, a total number of steps taken during a period of activity, or combinations thereof. Activity points may be derived from activity data information received by one or more sensors associated with system 100. As discussed in relation to FIG. 1-FIG. 5, one or more sensors may be located on, among others, a wrist-worn device 128/400, a shoe-mounted device 126, a body-mounted device 130a-130o, or a portable electronic device 112, or combinations thereof.

In one implementation, one or more elements of system 100 may execute one or more processes to calculate a total number of activity points earned by a user during a period of physical activity. For example, activity data information received from one or more sensors associated with a user may be communicated to server 111, wherein server 111 aggregates the activity data, and calculates a number of activity points associated with the activity data. In another example, one or more of devices 112, 114, 126, 128, or 130a-130o may receive sensor data, and calculate one or more activity points from the received sensor data. In another implementation, a cumulative number of activity points may be calculated by a remote device in system 100, and communicated to one or more of devices 112, 114, 126, 128, or 130a-130o through a network, such as BAN (102), LAN (104), or WAN (106), among others. Further, in one example, a device, such as one or devices 114, 126, 128, or 130a-130o, may be a unitary device/apparatus, and comprise a unitary body configured to accommodate one or more processors, sensors, user interfaces, and the like.

The calculation of energy expenditure may be performed using one or more different methodologies. Certain embodiments may classify physical motions of a user. For example, one or more activities may be classified. A system may process data received from one or more of the sensors described above to attempt to classify a user's activity. For example, a system may compare a sensor signal to one or more signal or activity "templates" or "signatures" corresponding to selected activities. In certain embodiments, templates may be created by attaching sensors to a user and monitoring signals generated when the user performs various activities. In accordance with certain embodiments, an activity may be associated with an activity template specific to user 124. In one such embodiment, user 124 may be assigned a default template for a specific activity unless a specific template has been assigned to that activity. Thus, user 124 may create or receive (but is not required to create or receive) an activity template that may be more accurate than a default template because the template is more specific to the user and/or the activity. User 124 may have the option to create templates for one or more predefined or undefined activities. A specific or otherwise new template might be shared among the community of users. Shared templates may be based on a variety of different sensors. In some embodiments templates may be refined or adjusted for use with different sensors. For example, a template that was created for use with a shoe based sensor may be refined for use with a wrist worn sensor.

An activity template may be created from data obtained from one or more of a plurality of different sensors. For example, a first group of sensors (e.g. sensors 126 and 128) may be utilized in the formation or refinement of a first activity template; however, a second group of sensors (e.g., sensors 138 and a sensor included in portable electronic device 112) may be utilized in the formation or refinement of a second activity template. In yet further embodiments, a third group of sensors, may be utilized in the creation of the first activity template for a second user (e.g., not user 124) than utilized for the formation of the same activity template as user 124. Thus, in accordance with certain embodiments, there is no requirement that data from a specific sensor be received for either: 1) the same activity template for different users; and/or 2) different activity templates for the same user.

In one embodiment, a wrist mounted accelerometer, which may be a multi-axis accelerometer, may be attached to a user and signal templates based on the accelerometer output when the user runs, walks, etc. may be created. The templates may be functions of the sensor(s) used and/or the locations of the sensor(s). In some embodiments, a single signal (or value) is created by combining multiple signals (or values). For example, three outputs of a three axis accelerometer may be summed or otherwise combined to create one or more signals. Example embodiments may include comparing a signal, multiple signals or a combination of signals to one or more templates. In some embodiments, a best match approach may be implemented in which every activity is attempted to be classified. In other embodiments, if a signal, multiple signals or combination of signals does not sufficiently match a template, the activity may remain unclassified. Some embodiments may utilize only templates for running and walking and a best first approach is used to determine whether the user is running or walking.

Certain embodiments may not categorize the user's activity or motions, such as into motion categories (e.g., running, walking, soccer), but rather determine energy expenditure without categorizing the data. In one implementation, training data may be used to construct one or more models, otherwise referred to as experts, or expert models, for predicting, among others, a volume of oxygen consumption based upon (at least in part) one or more individual-specific properties such as a gender, a mass and/or a height of a user. Accordingly, information from one or more sensors associated with a device, such as device 112, 126, 128, 130, and/or 400, may be used to calculate one or more attributes. In turn, the calculated attributes may be compared to attributes associated with one or more constructed models, and thereby, used to predict a volume of oxygen being consumed by a user while outputting motion signals (sensor output values) corresponding to the calculated attributes. For example, a user may be performing an activity, such as playing soccer, while wearing a sensor device on an appendage. The sensor device, in turn, may output sensor values, which may be processed to calculate one or more attributes. Subsequently, the one or more calculated attributes may be compared to one or more attributes associated with one or more models, and an estimation of a volume of oxygen being consumed by the user while playing soccer may be made. Furthermore, said estimation of a volume of oxygen being consumed may be used to estimate energy expenditure values by the user playing soccer.

In one implementation, portable electronic device 112 may display a GUI 600 communicating a total, or cumulative number of activity points 602 earned by a user during a specified time period 604. In another implementation, a user may interact with GUI 600 to receive information related to the earned number of activity points 602, wherein this related information may include one or more activity types carried out, or one or more locations at which the activities were carried out, among others. It will be readily apparent to one of ordinary skill that interaction with GUI 600 may be by any conventional means. For example, portable electronic device 112 may have a capacitive screen, and a user may interact with GUI 600 by touching one or more portions of the capacitive screen with one or more fingers. In other examples, interaction with GUI 600 may be via one or more control buttons. Furthermore, it will be readily apparent to those of skill that GUI 600 may additionally, or alternatively, be displayed on one or more devices 114, 126, 128, or 130a-130o, among others associated with system 100. It will further be understood that GUI 600 is an exemplary embodiment of a graphical user interface for conveying activity point information to a user, and other alternative embodiments of GUI 600 may be employed without departing from the scope of the disclosure described herein.

Figure 7:
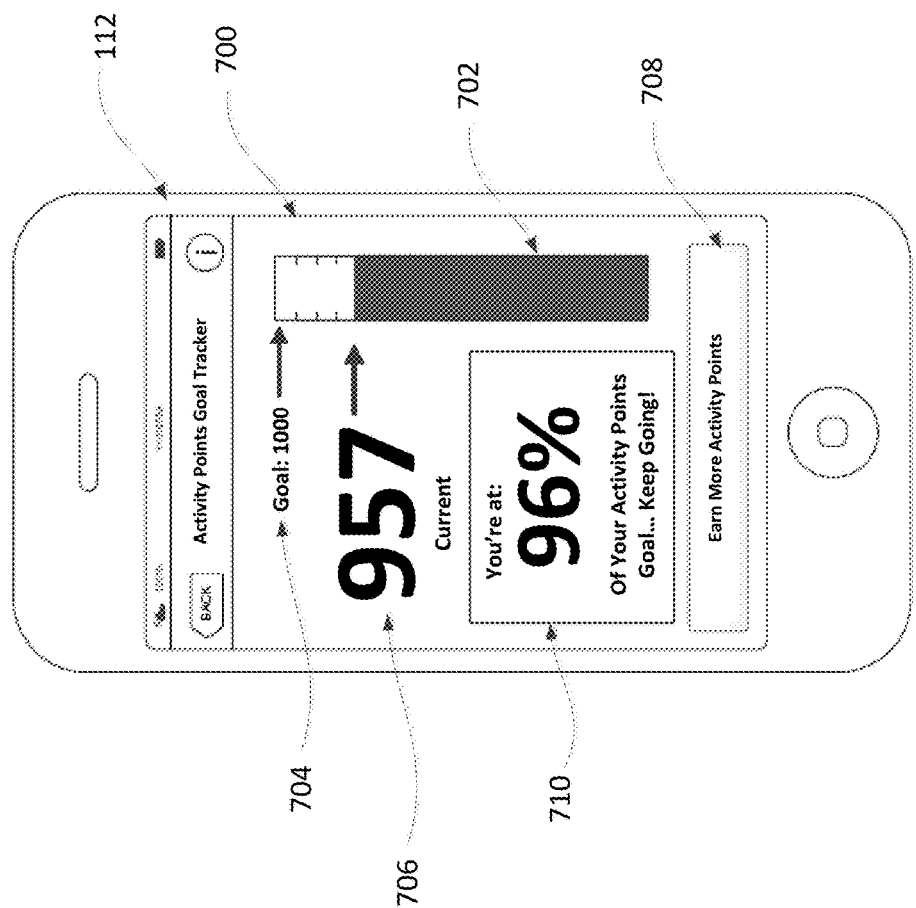
FIG. 7 is an example display of a graphical user interface for communicating activity points goal information to a user.

FIG. 7 is an example display of a GUI 700 for communicating activity points goal information (otherwise referred to as activity level goal information) to the user. Accordingly, GUI 700 may be used to motivate a user to increase his/her total amount of physical activity during a specified time period in order to reach one or more predetermined goal points. In one implementation, GUI 700 may be displayed on a portable electronic device 112, however, and as described in relation to GUI 600 from FIG. 6, GUI 700 may be displayed on one or more alternative, or supplementary devices from system 100. In particular, GUI 700 includes a goal status indicator 702. In one embodiment, the goal status indicator 702 is a bar chart that dynamically fills as the number of activity points earned by a user increases. In the exemplary embodiment of FIG. 7, the goal status indicator 702 includes a current number of activity points indicator 706, and a goal number of activity points indicator 704. However, it will be readily apparent to those of skill that the goal status indicator 702 may be embodied using any appropriate chart, symbol, or text to represent a relationship between a current cumulative number of physical activity points and a goal number of physical activity points. GUI 700 further includes message field 710 for communicating one or more points of information to the user related to his/her current cumulative activity points in relation to a goal number of activity points. In this way, message field 710 may be used to communicate one or more motivational messages/reminders to the user in order to encourage the user to continue to participate in one or more physical activities in order to meet prescribed goal number of activity points. The motivational messages communicated via message field 710 (otherwise referred to as reminder field 710) may include, among others, a percentage value corresponding to a ratio between a current cumulative number of activity points and a goal number of activity points when the percentage value is greater than, for example, 80%. In another implementation, a motivational message communicated via message field 710 may include a number of minutes of physical activity that may earn a number of activity points to reach a goal number of activity points, when the number of minutes is below a threshold, which may be, for example, 30 minutes. Furthermore, it will be readily apparent to those of skill that message field 710 may communicate a wide variety of alternative motivational messages to increase the likelihood that a user will continue participating in one or more physical activities in order to achieve a goal number of activity points over a predetermined time period. Additionally, message field 710 may be communicated to a user separately to other elements of GUI 700, such as goal status indicator 702.

GUI 700 may include interaction field 708, wherein upon selection, by a user, of interaction field 708, the user is presented with one or more suggestions for earning activity points to reach the goal number of activity points 704. These one or more suggestions are described in further detail with reference to FIG. 8.

Figure 8:
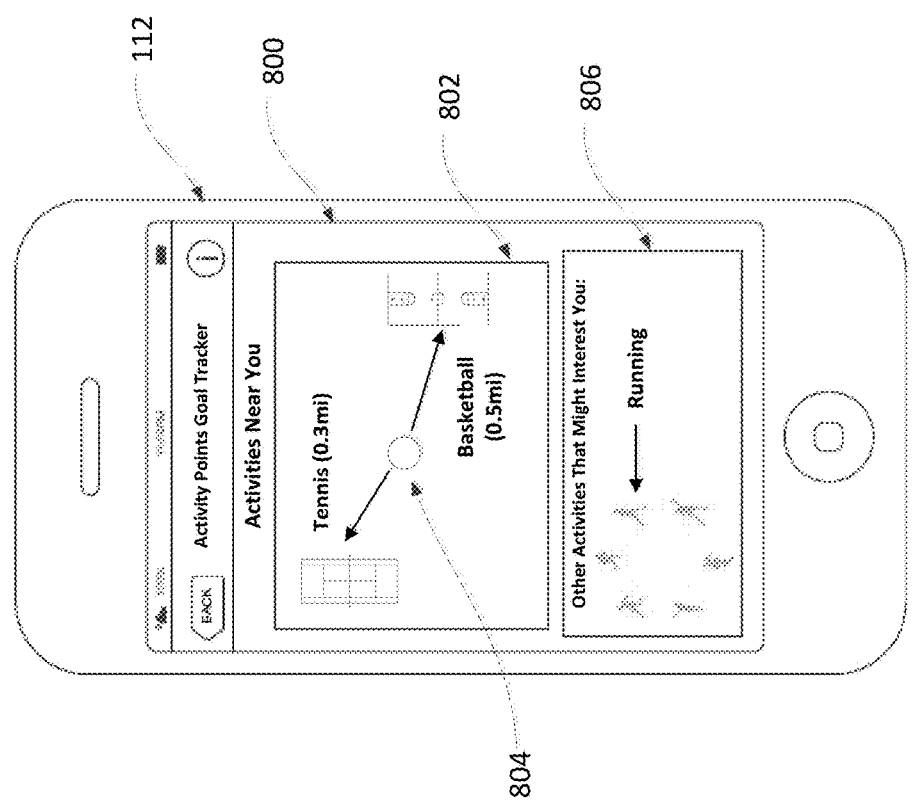
FIG. 8 schematically depicts an example display of a graphical user interface for communicating suggestions for earning activity points to meet an activity points goal.

FIG. 8 schematically depicts an example display of a GUI 800 for communicating one or more suggestions for earning activity points to meet an activity points goal. GUI 800 may, in one exemplary implementation, be displayed on a portable electronic device 112, however GUI 800 may alternatively be displayed on one or more devices 114, 126, 128, or 130*a*-130*o* associated with system 100, among others. GUI 800 may include a map of local activities 802, wherein map 802 may be generated based on location data received from a GPS sensor associated with portable electronic device 112. Map 802 may display a current location 804 at the map's center, and one or more nearby locations at which one or more activities may be performed. In the exemplary embodiment of FIG. 8, map 802 displays a tennis course that is 0.3 miles from the user's current location, and a basketball court that is 0.5 miles from the user's current location.

In one implementation, activities displayed on map 802 may be associated with one or more other individuals with whom the user of GUI 800 has a known relationship. These known relationships may be established, by system 100, by executing one or more processes to search one or more online social networks associated with user. In this way, one or more "friends" of the user may share their location and current activity with the user of GUI 800 through system 100. In another implementation, map 802 may suggest one or more activities within a predetermined distance of the user's current location based on user preferences for participation in one or more specific sports. In yet another implementation, map 802 may suggest one or more activities based on a number of participants, wherein the participants are unknown to the user. In this way, map 802 may suggest one or more locations for participating in "pickup" games (games involving participants who are unknown to the user), among others. In another embodiment, map 802 may display one or more locations associated with one or more activities based on athletic equipment in possession of the user. In this way, for example, when the user is wearing a pair of basketball sneakers, system 100 may suggest basketball-related activities via GUI 800, among others. Information regarding the type of sports equipment in possession of the user may be communicated via one or more sensors associated with system 100, such as one or more shoe-mounted devices 126, as described in relation to FIG. 1. In this way, one or more sensor-enabled pieces of sports equipment/devices may communicate a signal to portable electronic device 112 indicating that the user is in possession of equipment associated with one or more sporting/athletic activities. Alternatively, sports equipment associated with the user may be recorded by system 100 in memory, such as memory 202, and such that a database of sports equipment associated with the user is retained, based on data input by the user to the database, and wherein the sports equipment need not be sensor enabled. GUI 800 may further include information field 806 for suggesting one or more activities that may be performed by the user to earn activity points to meet an activity points goal, wherein the activities suggested in information field 806 may not be based on a proximity of one or more other individuals, or a sports facility, to the current location of the user. In this way, information field 806 may suggest one or more activities based on sports equipment in possession of the user. Information field 806, and map 802, may alternatively suggest one or more activities based on one or more activities performed by the user in the past, and recorded in memory, such as memory 202. Furthermore, it will be readily apparent to those of skill that information field 806, and map 802, may suggest one or more activities to a user based on a plurality of data types which may include, in addition to location data, data related to a number of participants and availability of sports facilities, and data related to the sports equipment available to the user, among others, suggestions based on user viewing habits, wherein GUI 800 may suggest one or more physical activities associated with sports that are watched by the user on television, or searched for by the user on the Internet, among others.

Furthermore, information field 806, and map 802, may indicate an estimated number of activity points that may be earned based on one or more durations of physical activity associated with the one or more activity-type suggestions. The one or more estimated number of activity points associated with one or more durations of physical activity may be based on a deficit number of activity points associated with the user in order to reach an activity points goal. For example, if a user requires fifty activity points to reach a daily activity points goal, the estimated number of activity points displayed by map 802, or information field 806, may be associated with durations of physical activity corresponding to approximately fifty activity points.

Figure 9:
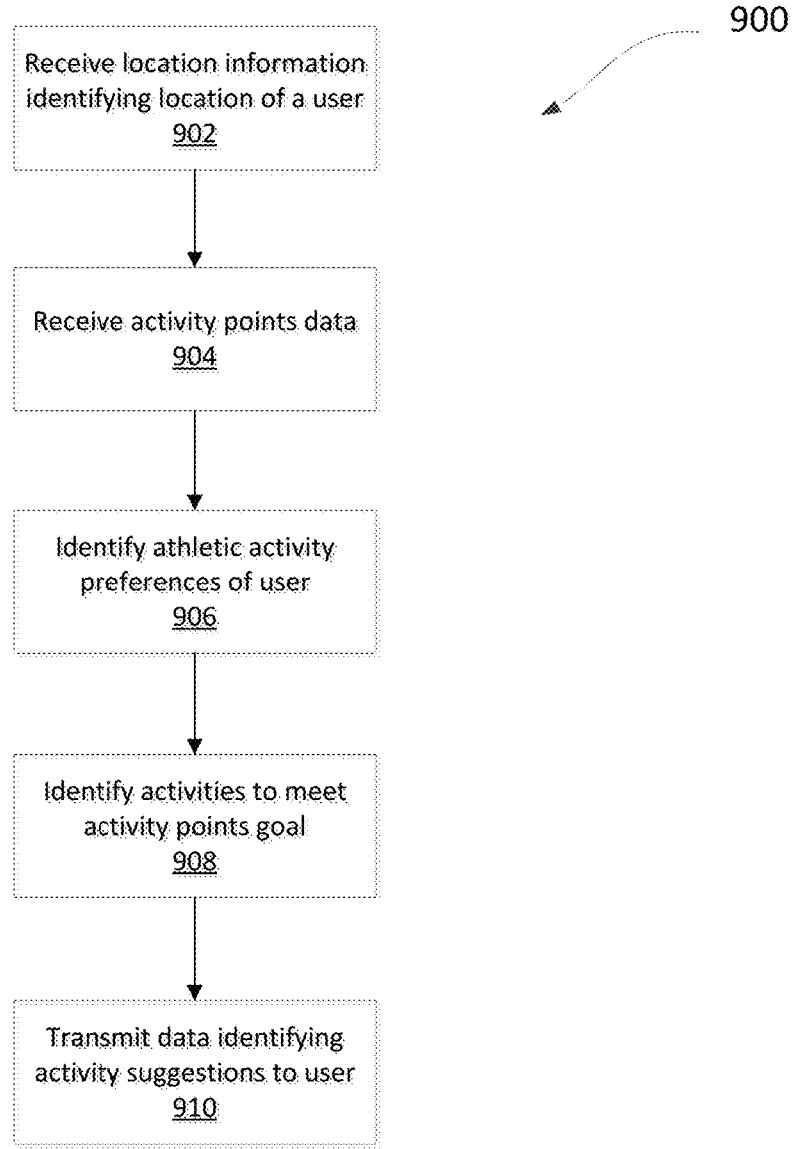
FIG. 9 is a flowchart diagram of an activity goal motivation process.

FIG. 9 is a flowchart diagram of an activity goal motivation process 900. Process 900 may be executed in order to suggest one or more physical activities to be performed by a user in order to earn activity points, or energy expenditure points, to meet a goal number of points for a given time period. This time period may be, among others, an hourly, daily, weekly, monthly, or yearly activity points goal, among others. Furthermore, process 900 may be executed by one or more devices associated with system 100, as described in relation to FIG. 1. In the disclosure that follows, process 900 will be described in relation to a portable electronic device 112, however one of ordinary skill will understand that process 900 may be executed by a plurality of different devices, such as devices 114, 126, 128, or 130*a*-130*o* associated with system 100.

Process 900, at block 902, receives location information that identifies a current location of a user. As described in relation to FIG. 6 and FIG. 7, this location information may be received from a GPS sensor associated with a portable electronic device 112. However, in other implementations, location information may be received based on an IP address associated with an Internet connection to portable electronic device 112, a radio signal associated with cellular communication to portable electronic device 112, or a user input to portable electronic device 112 specifying a geographic location, among others. At block 904, process 900 receives data related to a cumulative number of activity points earned by the user during a specified time period, wherein the earned number of activities points correspond to the total amount of physical activity carried out by the user. Alternatively, and at block 904, process 900 may determine, or calculate one or more activity points earned by the user based on activity data received from one or more sensors, wherein the one or more sensors may be associated with one or more of devices 112, 114, 126, 128, or 130*a*-130*o* from FIG. 1. Additionally, at block 904, process 900 may receive data related to an activity points goal, wherein an activity points goal corresponds to a target amount of physical activity to be performed by the user during a specified time period. Block 904 may include a calculation of a deficit number of activity points corresponding to the numerical difference between the activity points goal and the current cumulative number of activity points earned by the user.

Accordingly, in one example, a number of activity points may be determined/calculated, based on sensor data generated as a result of physical motion of a user over a first time period. This determination may be carried out at, in one example, block 904 of process 900. Further, this number of activity of activity points may be added to a cumulative number of activity points accrued by the user from a starting time point. Additionally, the number of activity points earned/accrued over the first time period may be compared to a goal activity point total, wherein the goal activity point total may be associated with a second time period. As such, in one specific example, a starting time may be t=0 seconds. The first time period may be 10 seconds. The second time period may be 30 seconds, which would span t=0 seconds to t=30 seconds, and wherein the 10 second first time period is encompassed within the second period, e.g. from t=8 seconds to t=18 seconds, and the like. Those of ordinary skill in the art will understand that the specific time period durations should not limit this disclosure, and that the first period, second period, and starting time point may be any length of time, or any time of day, and the like.

Block 906 of process 900 identifies one or more user preferences associated with athletic activities. These user preferences may include information related to other individuals known to the user participating in one or more athletic activities. For example one or more individuals known to the user may communicate their location and an athletic activity currently being performed, such that the user has an opportunity to join into an organized game associated with a particular sport, among others. The user preferences may further include information related to athletic activities performed by the user in the past. In this way, system 100 may retain a database, in memory 212, of sports of interest to the user. Furthermore, the user preferences may be based on athletic equipment owned by, worn by, or in possession of the user. In this way, system 100 may retain a database, in memory 212, of activities of interest to the user based on products owned/in possession of the user.

Block 908 identifies one or more activities that may be performed by the user to meet the activity points goal. This identification may be based upon the calculation of an activity points deficit between the activity points goal and the current cumulative number of activity points earned by the user, in addition to the established location of user, and the identified activity preferences associated with the user. In this way, block 908 may identify one or more athletic activities that may be performed by the user within a predetermined range/proximity of the current location of user. In alternative embodiments, however, block 908 may identify one or more activities that may be performed by the user in order to reach the activity points goal, wherein the identified activities are not based upon a proximity to the user's current location.

In one example, block 908 may identify one or more activities that may be performed by the user to meet an activity point goal of an activity session. As such, block 908 may include calculating a difference (deficit) between an energy expenditure metric for a current activity session and an energy expenditure metric for a previous activity session for a same athletic activity, among others.

At block 910, system 100 may transmit data identifying activity suggestions to the user. In one embodiment, these suggestions may be communicated to the user via a graphical user interface, such as GUI 800 from FIG. 8. The information communicated to the user may be ordered, or ranked, such that, among others, physical activities known to be of greater interest to the user are preferentially displayed to the user. For example, process 900 may determine, based on a number of occasions during which the user participated in basketball games, that the user has a preference for the sport of basketball. In response, process 900, at block 910, may preferentially display activity suggestions related to basketball. In this way, process 900 may be more likely to motivate the user to participate in further physical activity in order to reach the predetermined activity points goal. In another implementation, process 900 may rank activity suggestions based on estimated activity durations to make up the user's cumulative number of activity points to the activity points goal. As such, a motivational message to a user may rank one or more physical activities based on a likelihood that there will be enough time within an activity period to earn enough activity points to reach an activity goal for the activity period. In one example, the activity period may be a half hour, an hour, a day, a week, or a month, or any other period of time. In one example, the ranking of the one or more physical activities may be carried out by a processor within a unitary device, such as devices 114, 126, 128, or 130a-130o. Accordingly, in one example, the ranking may determine a probability (likelihood) that a given physical activity can be participated in by a user and result in a number of activity points being earned (calculated/awarded to the user etc.) to meet an activity points goal. This probability may be based on a proximity of the user to a sporting facility to carry out one or more physical activities, an amount of time left in an activity period during which an activity points goal is to be met, and a record of physical activities carried out by the user in the past, among others. In this way, based on the record of physical activities carried out by the user over a previous time period, the probability may favor (rank more highly) a first activity for which the user consistently earns a first amount of activity points, over a second activity for which the user earns a second, significantly variable amount of activity points. In one specific example, the ranking may rank a first activity, for which the user consistently earns 100+/−10 activity points per hour higher than a second activity for which the user, from a record of user activity, earns 110+/−90 activity points per hour, and the like.

In addition, block 910 may communicate one or more points for information in order to motivate the user to continue with physical activity in order to meet the activity points goal. These points of information may include a description of the user's current cumulative number of activity points in relation to the goal number of activity points, or one or more estimated time durations that would be sufficient to make up the deficit between the current cumulative number of activity points and the activity points goal, among others.

The process 900 may be implemented in an activity monitoring device. Such an activity monitoring device may be a general purpose computer or mobile device which is configured to operate as an activity monitoring device or may be a device designed specifically for this function.

The activity monitoring device may have a context identifying module which is configured to determine or receive information regarding the location of the user (block 902) and/or the athletic activity preferences of the user based on, for example, the athletic equipment in possession of the user (block 906).

The activity monitoring device may further comprise a deficit determining module which calculates the deficit number of activity points in block 904.

An activity suggestion module may transmit data identifying activity suggestions to the user in block 910 based on the deficit determined by the deficit determining module and information provided by the context identifying module regarding the location and/or athletic activity preferences of the user.

Context information may be derived based on the situation of the user (i.e. relating to location, preferences, equipment resources, etc.). The context information can be used to suggest suitable activities for the user to achieve their activity points goal. This is performed automatically or semi-automatically and thus avoids the need for the user to carry out extensive research into suitable activities. A user may therefore be able to more quickly identify suitable activities, with minimal input directly from the user. Accordingly, data throughput and power consumption of the associated device may be reduced. Further, as the data input requirements are reduced, the device need not have such a complicated input system. This may reduce the complexity, cost, reliability, durability, and/or power consumption of the device.

In any of the above aspects, the various features may be implemented in hardware, or as software modules running on one or more processors. Features of one aspect may be applied to any of the other aspects.

There may also be provided a computer program or a computer program product for carrying out any of the methods described herein, and a computer readable medium having stored thereon a program for carrying out any of the methods described herein. A computer program may be stored on a computer-readable medium, or it could, for example, be in the form of a signal such as a downloadable data signal provided from an Internet website, or it could be in any other form.

Sessions

Alternative embodiments of the invention may use alternative or additional equations for calculating point values and/or other quantities. The equations may include derivations of measured and/or calculated values. Derivations that include time periods may be used to show rates and rates of change. For example, one equation may be used to determine a rate of accumulating activity points or energy expenditure points. Another equation may be used to determine a quantity of activity points or energy expenditure points accumulated over a predetermined time period.

Some equations may use variables other than time. For example, some equations may be used to calculate a value as a function of activity points or energy expenditure points and steps. Calculating values that are functions of activity points or energy expenditure points and other variables may be used to compare the efficiencies of various activities. For example, an equation may be used to determine that taking steps at a faster pace may result in activity points or energy expenditure points accumulating at a faster per step pace. Another exemplary equation may determine activity points or energy expenditure points per a predetermined distance or a unit of distance.

Some equations may be used to calculate first and/or second derivatives of measured or calculated values to show rates and rates of change. For example, an equation may be used to calculate or estimate a rate of accumulation of activity points or energy expenditure points at a given time. In some embodiments an instantaneous rate of accumulation of activity points or energy expenditure points is displayed to a user via display 235 or a display that is part of a mobile device.

After the energy expenditure points are calculated, the calculated points may be combined, such as being added, to a total in step 612. The total may allow user 124 (and/or selected individuals or groups approved by user 124) to see how many points are earned over various periods of time, such as days, weeks and months. Totals may also be calculated for multiple time periods. For example, a user may receive totals for periods that include 24 hours, one week, one month and one year. In some embodiments users may select other time periods or deselect time periods. A user may track multiple time periods concurrently and track points award since the beginning of use of a device or start of a program. The total for any giving time period may represent points earned for several activities. For example, in a day a user may receive points for walking, jogging and sprinting during different time periods. As mentioned above, the points earned for each activity may be a function of a corresponding activity factor.

As indicated above, systems and methods may be variously implemented to determine a rate that a user accumulates activity points or energy expenditure points. In one embodiment, energy expenditure intensity values may be calculated for one or more time periods. The plurality of time periods may be within a unitary time frame, such as a minute, 5 minutes, 10 minutes, an hour, or a day. Those skilled in the art will appreciate that these are merely examples. In certain embodiments, a user may designate or alter the duration and/or quantity of time periods and/or time frame.

Certain embodiments may organize data collected at different time periods into a collection. As one example, data collected during time periods within a time frame may be designated as a "session". For example, a UI may be configured to permit a user to designate past activity data as being associated with a specific activity, sport, event or motion. In one embodiment, a user may indicate that past activities (which may be stored as raw and/or processed data, including for example, energy expenditure points or values) were collected during a soccer game or running session. As another example, an input may designate that future activities, such as a scheduled soccer game or running event, is a "session" or collection of related data. One or more designations may be suggested or even automatically generated from electronic data, such as information stored in relation to a calendar application on an electronic device. The electronic data may be stored on the same device comprising a sensor from which at least a portion of the motion data is collected from and/or configured to receive data from at least one of the sensors.

In another embodiment, motion data collected within a geographic area may be used to associate that data with a specific sport or activity. For example, GPS data (which may be obtained from the same or different device that obtains at least a portion of the motion data) may be utilized to determine that the user is or was within a geographic area. Thus, data collected within that area may be associated together as a session or other collection. In yet another embodiment, a combination of information may be used to designate a collection of motion data, such as a session. In one embodiment, motion data obtained at or within a proximity to a geographic location or area during or more time frames (e.g., data collected within 500 feet of a soccer field during the hours of 2-4 pm on a Saturday) may be associated together, such as classified as a soccer session. Geographic data may be obtained from GPS, triangulation of communication signals, presence of other signals, such as detection of a certain sensor, and/or by manual indication via a user input.

Motion data, such as the data described above or anywhere throughout this disclosure, may only be classified as a session if at least a portion of the data meets a criterion. For example, if energy expenditure intensity values for at least a portion of the activity does not meet a threshold, then a portion or all of the data may not be classified within a session. Users may be able to tag the sessions as being within certain activity, either during or after collection of the data.

Energy expenditure values, including energy expenditure intensity values, may be displayed, such as on a portable electronic device, as a function of time. In one implementation, data of a session may be displayed. A first value collected during a first time period may be displayed as a first variation of a display characteristic based upon exceeding a first threshold and a second value (which may be collected during a second time period within the same session) may be displayed as a second variation of the display characteristic based upon exceeding the second threshold. The display characteristic may relate to at least one of: color, size, or shape, for example.

Further embodiments may organize similar collections of data, such as session data, together. For example, "soccer sessions" may be organized such that a user may readily view trends from different sessions, which may be collected from motion data of different times and/or locations. Further, a first session may have been collected by one or more sensors that were not utilized to obtain motion data during another session. One or more sessions may be designated by markers on a map.

In one embodiment, one or more calculations of the motion data may occur in real-time, or as the data is being collected. In one embodiment, energy expenditure values may be displayed on an output of an electronic device. In one embodiment, an accumulation of energy expenditure values may be displayed and other information, such as color variations may indicate an intensity level, such as based upon the quantity of energy expenditure of the user as a function of time.

One or more processes for calculating energy expenditure values, intensity values, and/or other values may be based, at least in part, on the designation of the data. For example, if a session is designated as a yoga session, a first process may be used to calculate energy expenditure, whereas a designation of a soccer game may result in a different process for calculating energy expenditure. Designations may be based upon the user input, sensor data, location, and/or one or more other factors. Further, the designation may result in utilizing (or not utilizing) one or more sensors. One or more collections of data may be re-designated. In certain embodiments, re-designation may result in recalculating at least a portion of the data, such as by using different sensor data, and/or different equations for calculating the values.

Further aspects relate to systems and methods that permit access of a plurality of users to at least a portion to other user's energy expenditure, including for example access to session data of other users. For example, players in a basketball or soccer league may want to compare their energy expenditure levels among teammates and/or one or more opposing players. A collection of motion data (such as session data) may be shared within one more groups. Groups may be implemented such that only a portion of session data (e.g., data collected during a specific time, by a certain sensor, occurring at a certain area, etc.) may be shared with one or more users. Those skilled in the art will appreciate that one or more criteria may dictate sharing properties. Users may create groups, such that an invite from a specific individual or groups of individuals is required for access to certain information. A user may belong to multiple groups and as such, the same or different portions of their activity data (or derivatives thereof) may be shared with different people. A group may provide rankings based upon, for example, total time within sessions, total energy expenditure, energy expenditure meeting specific criterion (e.g., locational criterion), intensity, distance, etc. Further, one or more members of the group may set a group goal, such as earning a specific quantity of energy expenditure during a time period or total time of activity meeting a certain threshold, for example. The goal may permit members to compete against each other to meet a goal, and/or permit at least two members to cooperatively meet one or more goals.

As discussed above, certain embodiments disclosed herein relate to calculating an energy expenditure intensity value. As one example, this value may be determined by quantifying the energy expenditure values for a user for a certain time period. For example, energy expenditure values (or derivatives thereof) a span of time may be used to determine an energy expenditure intensity value for that span of time. Motion data may be obtained from a plurality of different time periods within the time frame. For example, data from a first sensor (which may be an accelerometer, for example) may be obtained every second or multiple times a second and data from a second sensor (such as a force sensor) may be obtained for the same, different or partially overlapping time periods. For example data from the second sensor may be collected at ½ the rate of the first sensor. Data collected at these time points may be used to determine energy expenditure values for specific time periods within the time frame. The time frame is not required to be static. For example, the time period may be rolling consecutive duration of time. Yet, in other embodiments, the time frame may be static.

Certain embodiments may determine whether one or more energy expenditure intensity values meet a threshold during the time frame. Further embodiments may permit one or more users to compete which user or groups of users obtained more energy expenditure during one or more periods. In one embodiment, if a first user meets an intensity threshold level for a duration and a second user does not meet the intensity threshold level for that duration, the first user may be deemed a winner of that duration. If both users met the threshold level, then a tie may be declared. In another embodiment, total energy expenditure over a larger period of time of time that includes the duration(s) in which both users met the threshold level) may be used to determine a winner. In yet other embodiments, whichever user obtained a higher intensity level during the duration or the larger time period of time may be used to determine a winner. Certain embodiments may not utilize data from other actual users. In certain implementations, a virtual AI user may be utilized. Further embodiments may not utilize data from other users, virtual or real, but rather, a user's performance, such as meeting a goal and/or obtaining a virtual reward, may be based solely on whether they achieve a set threshold, regardless of what other user's data indicates and/or if there is not any other user data for comparison. In this regard, the competitions and/or group activities described herein, may be "won" or at least competed in by a single user. For example, a user can "win the day" by obtaining a threshold quantity of hours or time frames in which they met a threshold intensity level. Thus, all disclosure herein relating to comparing a first user's data to a second user's data also is intended to disclose comparing a first user's data to electronically stored data that may not have been collected from actual activity data of another user.

In one embodiment, it may be quantified how many times a user meets a threshold intensity level for a time frame (such as an hour or a day). Systems and methods may be implemented to quantify the number of times a plurality of users each meet a threshold within a set time, such as within with a day. Certain methods may be configured to permit users to compete for instances of meeting a threshold level of intensity in a day or other length of time. As one exemplary embodiment, it may be determined whether any of a plurality of users obtained an intensity threshold level a set amount of time. If a user meets the threshold level for any set duration, which may be measured by ensuring they have a plurality of consecutive expenditure values, then they may get credit for a longer period of time. The quantity of threshold intensity levels meet for the specified durations may be quantified and one or more users may be ranked or otherwise compared. For example, a user may "win the day" if that user met more threshold levels than another user or above a threshold quantity. As discussed above, one or more tie-breakers may be used. Further, as discussed throughout this disclosure, certain criterion may be used to determine whether sensor data is considered and/or how it may be processed. Further, although an exemplary threshold level was discussed, those skilled in the art will appreciate that multiple threshold levels may be used. In one embodiment, a higher threshold intensity level may be weighted in ranking and/or determining a winner.

Further aspects relate to notifying a user when they have or have not met a threshold level or levels. For example, a device may be configured to motivate a user to conduct activity if they have not hit a threshold level for a duration of time. Similarly, a notification may be provided to indicate that they are unlikely to meet a threshold level, such as for a duration of time that includes the current time the user is intended to get the notification. A second reminder, which may be the same or different from the first reminder, could be provided again when less time remains. In one embodiment, the notification may be configured to be generated on a device that comprises at least one sensor that created at least a portion of the user's motion data. In one embodiment, the device may be configured to be worn on an appendage, such as for example, on a user's arm, wrist, or leg. The device may comprise at least one accelerometer for obtaining motion data. In further embodiments, the device may not only generate the notification, but also configured to provide the notification, such as through a display, audio, tactile feedback (e.g., vibrations) and combinations thereof. In other embodiments, the notification may be generated on a first device, such as a computer or portable electronic device and transmitted to a device having at least one of the sensors used to collect the data.

Further aspects relate to motivating users to reach an intense level of motion. For example, certain embodiments may determine how much time a user is engaged within a highly intense activity. As one example, certain embodiments may only quantify total intensity by quantifying time periods or time frames that meet at least one threshold of energy expenditure intensity. For example, time conducted performing an activity that provides energy expenditure intensity values less than a first threshold may not be utilized. Other embodiments may utilize data meeting a plurality of thresholds. In one embodiment, time in which a user is accumulating at least a threshold quantity of energy expenditure points, which may or may not be directly or indirectly derived from calories, is marked as an intense period of time.

In one embodiment, time in which a user is accumulating at least a threshold quantity of energy expenditure points, which may or may not be directly or indirectly derived from calories, is marked as an intense period of time. As one example, minutes in which a user earned (or is earning) at least 18 Nike FUEL points per minute may be totaled. If the number of minutes reaches a threshold amount, such as for example, 30 minutes per day or week, then the user may be provided a virtual award. In accordance with one embodiment, Total intensity=moderate (18-27 Nike FUEL points per minute)+high (28+Nike FUEL points per minute). Certain embodiments may have a challenge for the user to conduct activity that provides at least a threshold level of energy expenditure intensity for at least 30 minutes for one or more instances. In one embodiment, the instances may be 3 or more instance of at least 30 minutes per week.

Furthermore, the present application extends to the subject-matter described in the following numbered clauses.

Clause 1: An activity monitoring device comprising: a context identifying module configured to obtain information regarding a location of a user and/or athletic equipment in possession of the user; a deficit determining module configured to determine a deficit between a level of activity performed by the user and a goal level of activity; and an activity suggestion module configured to suggest, based upon the determined deficit and the information obtained by the context identifying module, one or more activity types to be carried out by the user to reach the goal level of activity.

Clause 2: An activity monitoring device as described in Clause 1, wherein the activity suggestion module is further configured to rank the one or more activity types based on activity preferences of the user.

Clause 3: An activity monitoring device as described in Clause 2, wherein the activity preferences are based on a number of previous occasions during which the user participated in one or more activities.

Clause 4: An activity monitoring device as described in Clause 2 or 3, wherein the activity preferences are based on a number of individuals known to the user, and participating in an activity.

Clause 5: An activity monitoring device as described in any of Clauses 2 to 4, wherein the activity suggestion module is further configured to calculate an estimated time duration to reach the goal level for the or each activity type, the activity suggestion unit ranking the activity types based on the calculated time durations.

Clause 6: An activity monitoring device as described in any preceding Clause, wherein the activity suggestion module is configured to suggest activity types in proximity to the location of the user.

Clause 7: An activity monitoring device as described in any preceding Clause, wherein the context identifying module is configured to determine the athletic equipment in possession of the user based on one or more signals received from sensor-enabled athletic equipment.

Clause 8: An activity monitoring device as described in any preceding Clause, wherein the context identifying module is configured to determine the athletic equipment in possession of the user based on a stored database of athletic equipment in possession of the user.

Clause 9: A computer-implemented method of operating a device comprising: obtaining context information regarding a location of a user and/or athletic equipment in possession of the user; determining a deficit between a level of activity performed by the user and a goal level of activity; and based upon the determined deficit and context information, suggesting one or more activity types to be carried out to reach the goal level of activity.

Clause 10: A computer-implemented method as described in Clause 9, further comprising: ranking the one or more activity types based on activity preferences of the user.

Clause 11: A computer-implemented method as described in Clause 10, wherein the activity preferences are based on a number of previous occasions during which the user participated in one or more activities.

Clause 12: A computer-implemented method as described in Clause 11, wherein the activity preferences are based on a number of individuals known to the user, and participating in an activity.

Clause 13: A computer-implemented method as described in any of Clauses 9 to 12, wherein the activity types are ranked based on one or more estimated time durations to reach the goal level of activity.

Clause 14: A computer-implemented method as described in any preceding Clause, wherein the athletic equipment in possession of the user is determined based on one or more signals received from sensor-enabled athletic equipment.

Clause 15: A computer-implemented method as described in Clause 14, wherein the athletic equipment in possession of the user is determined based on a stored database of athletic equipment in possession of the user.

Clause 16: A non-transitory computer-readable medium comprising executable instructions that when executed cause a computer device to function as an activity monitoring device as described in any of Clauses 1 to 8 or to perform the method as described in any of Clauses 9 to 15.

Further embodiments are provided below as exemplary clauses:

Clause 17: A computer-implemented method of operating a device comprising: receiving, at a processor included in the device, location information identifying a location of a user; determining, by the processor, a deficit between a level of activity performed by the user and a goal level of activity; and based upon the determined deficit, suggesting one or more activity types in proximity to the user to be carried out to reach the goal level of activity.

Clause 18: The computer-implemented method of Clause 17, further comprising: ranking, by the processor, the one or more activity types based on activity preferences of the user.

Clause 19: The computer-implemented method of Clause 18, wherein the activity preferences are based on a number of previous occasions during which the user participated in one or more activities.

Clause 20: The computer-implemented method of Clause 18, wherein the activity preferences are based on a number of individuals known to the user, and participating in an activity.

Clause 21: The computer-implemented method of Clause 18, wherein the activity types are ranked based on one or more estimated time durations to reach the goal level of activity.

Clause 22: A non-transitory computer-readable medium comprising computer-executable instructions that when executed by a processor is configured to perform at least: determining, by the processor, a deficit between a level of activity performed by a user and a goal level of activity; determining, by the processor, athletic equipment in possession of the user; and based upon the determined deficit and the athletic equipment in possession of the user, suggesting, by the processor, one or more activity types to be carried out by the user to reach the goal level of activity.

Clause 23: The non-transitory computer-readable medium of Clause 22, wherein the processor determines the athletic equipment in possession of the user based on one or more signals received from sensor-enabled athletic equipment.

Clause 24: The non-transitory computer-readable medium of Clause 22, wherein the processor determines the athletic equipment in possession of the user based on a stored database of athletic equipment in possession of the user.

Clause 25: The non-transitory computer-readable medium of Clause 22, further comprising: receiving, at the processor, location information identifying the location of the user, wherein the suggested activity types are further ranked based on proximity to the user.

What is claimed is:

1. A unitary apparatus configured to be worn by a user, comprising:
   a processor;
   a sensor configured to capture motion data and detect a geographic location of the user;

a user interface; and a non-transitory computer-readable medium comprising computer-executable instructions that when executed by the processor perform at least: detecting a current location of the user;

capturing, from the sensor while being worn on the user, motion data generated by the sensor as a result of a motion of the user;

calculating, from the motion data, an energy expenditure metric indicative of an amount of physical activity carried out by the user;

communicating, using the user interface, based on the detected current location of the user, a motivational message to the user that includes a dynamic goal status indicator and encourages the user to participate in an athletic activity, wherein the motivational message includes a map indicating a location within a predetermined range of the user at which one or more group activities can be participated in by the user, the map may suggest one or more activities based on a number of participants, where the participant are unknown to the user, and wherein the motivational message includes a probability that participating in the one or more activities will meet or exceed an energy expenditure goal, based on a record of physical activities carried out by the user in the past.

2. The unitary apparatus of claim 1, wherein the non-transitory computer-readable medium further comprises computer-executable instructions that when executed by the processor, perform at least:

calculating a difference between the energy expenditure metric for a current activity session and an energy expenditure metric for a previous activity session for a same athletic activity;

determining that the calculated difference is less than a threshold amount; and using the determination that the calculated difference is less than the threshold amount in generating the motivational message.

3. The unitary apparatus of claim 1, wherein the motivational message encourages the user to exceed an energy expenditure metric for a previous activity session.

4. The unitary apparatus of claim 1, wherein the motion data is generated during a sports game.

5. The unitary apparatus of claim 1, wherein the user interface is a display screen.

6. The unitary apparatus of claim 5, wherein the motivational message is communicated as a text message on a graphical user interface displayed on the display screen.

7. The unitary apparatus of claim 6, wherein the motivational message is displayed as a separate graphic on the display screen.

8. The unitary apparatus of claim 1, wherein the motivational message indicates an amount of time participating in the one or more group activities to reach an energy expenditure metric for a previous activity session.

9. The unitary apparatus of claim 2, wherein the energy expenditure metric for the current activity session and the energy expenditure metric for the previous activity session are based on a number of calories burned by the user.

10. The unitary apparatus of claim 2, wherein the energy expenditure metric for the current activity session and the energy expenditure metric for the previous activity session are based on a distance traveled by the user.

11. The unitary apparatus of claim 2, wherein the sensor comprises a heart rate monitor, and the energy expenditure metric for the current activity session and the energy expenditure metric for the previous activity session are based on a heart rate of the user.

12. The unitary apparatus of claim 1, wherein the apparatus is configured to be worn on an appendage of the user.

13. An apparatus, comprising:

a processor;

a sensor configured to capture motion data and detect a geographic location of a user of the apparatus;

a user interface; and memory storing computer-readable instructions that, when executed by the processor, cause the apparatus to:

detect a current location of the user;

capture motion data from the sensor;

receive an identification of an athletic activity being performed by the user during the capture of the motion data;

calculate an intensity level of the user during performance of the athletic activity from the motion data;

determine a deficit between the calculated intensity level and a previous intensity level of a user for the same identified athletic activity; and communicate, based on the detected current location of the user, a motivational message to the user if the deficit is less than a threshold value, wherein the motivational message includes a dynamic goal status indicator and a map indicating a location within a predetermined range of the user at which one or more group activities can be participated in by the user, the map may suggest one or more activities based on a number of participants, where the participant are unknown to the user, and wherein the motivational message includes a probability that participating in the one or more activities will meet or exceed the previous intensity level, based on a record of physical activities carried out by the user in the past.

14. The apparatus of claim 13, wherein the calculated intensity level is an energy expenditure over a discrete time period.

15. The apparatus of claim 14, wherein the time period is one hour.

16. The apparatus of claim 14, wherein the time period is one day.

17. The apparatus of claim 13, wherein the motivational message is communicated to the user on a graphical user interface generated by the processor for display on the user interface.

18. The apparatus of claim 13, wherein the motivational message includes a recommendation of an amount of time participating in the one or more group activities to reach the previous intensity level.

19. A non-transitory computer-readable medium comprising computer-executable instructions that when executed by a processor are configured to perform at least:

capture sensor data generated by a sensor as a result of a motion of a user;

detect a current location of the user;

calculate, from the captured sensor data, an intensity level as an energy expenditure over a specified amount of time for the user performing an athletic activity; and communicate a motivational message to the user when the calculated intensity level is within a threshold amount of a previously-stored intensity level for a same athletic activity, wherein the motivational message includes a map indicating a location within a predetermined range of the user at which one or more group activities can be participated in by the user, the map may suggest one or more activities based on a number of participants, where the participant are unknown to the user, and wherein the motivational message includes a probability that participating in the one or more activities will meet or exceed a previously-stored intensity level, based on a record of physical activities carried out by the user in the past.

20. The non-transitory computer-readable medium of claim 19, wherein the motivational message includes a suggested amount of time participating in the one or more group activities to exceed the previously-stored intensity level.

* * * * *